United States Patent
Willis

(10) Patent No.: US 6,896,657 B2
(45) Date of Patent: May 24, 2005

(54) METHOD AND SYSTEM FOR REGISTERING ULTRASOUND IMAGE IN THREE-DIMENSIONAL COORDINATE SYSTEM

(75) Inventor: Parker Willis, Atherton, CA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 95 days.

(21) Appl. No.: 10/444,165

(22) Filed: May 23, 2003

(65) Prior Publication Data

US 2004/0236220 A1 Nov. 25, 2004

(51) Int. Cl.⁷ .................................................. A61B 8/00

(52) U.S. Cl. ...................................................... 600/437

(58) Field of Search ................................. 600/407–472; 73/525, 526; 367/7, 11, 130; 128/916

(56) References Cited

U.S. PATENT DOCUMENTS

| | | |
|---|---|---|
| 4,549,533 A | 10/1985 | Cain et al. |
| 5,113,706 A | 5/1992 | Pittaro |
| 5,152,290 A | 10/1992 | Freeland |
| 5,321,501 A | 6/1994 | Swanson et al. |
| 5,329,929 A | 7/1994 | Sato et al. |
| 5,357,964 A | 10/1994 | Spivey et al. |
| 5,360,007 A | 11/1994 | Shinomura et al. |
| 5,373,845 A | 12/1994 | Gardineer et al. |
| 5,383,874 A | 1/1995 | Jackson et al. |
| 5,435,310 A | 7/1995 | Sheehan et al. |

(Continued)

FOREIGN PATENT DOCUMENTS

WO     WO 01/06917 A1     2/2001

OTHER PUBLICATIONS

Diagnostic Imaging Scan, Phillips prepares to launch system upgrade capable of true real–time 3D echo, General Collection W1 D1258iH, United Business media, V. 16, No. 18, Sep. 11, 2002.

Robert Lang, et al "A Fantastic Journey: 3D Cardiac Ultrasound Goes Live" Radiology Management, V. 24, No. 6, Nov./Dec. 2002.

N. Parker Willis, "Dynamically Alterable Three–Dimensional Graphical Model of Body Region", U.S. patent application No. 09/128,304, filing date Aug. 3, 1998.

(Continued)

*Primary Examiner*—Ali Imam
(74) *Attorney, Agent, or Firm*—Bingham McCutchen LLP

(57) ABSTRACT

The present invention provides systems, methods, and devices for imaging an internal anatomical structure. Ultrasound image data of the anatomical structure is acquired within a first coordinate system, and graphical data (e.g., sites of interest) is acquired in a second coordinate system. The location of an ultrasound transducer within the first coordinate system and a second coordinate system is determined, and a transformation between the first and second coordinate systems is then performed based on the location of the ultrasound transducer within the first and second coordinate systems. Using this transformation, the ultrasound image data, which has previously been acquired in the first coordinate system, can be registered and displayed within the second coordinate system, along with graphical data. Or the graphical data, which has previously been acquired in the second coordinate system, can be registered and displayed within the first coordinate system, along with the image data. In this manner, the image and graphical data can be easily displayed together independent of any movement by the imaging device that acquires the image data.

48 Claims, 9 Drawing Sheets

U.S. PATENT DOCUMENTS

| | | | |
|---|---|---|---|
| 5,460,178 | A | 10/1995 | Hudon et al. |
| 5,471,989 | A | 12/1995 | Roundhill et al. |
| 5,485,849 | A | 1/1996 | Panescu et al. |
| 5,494,042 | A | 2/1996 | Panescu et al. |
| 5,779,641 | A | 7/1998 | Hatfield et al. |
| 5,787,889 | A | 8/1998 | Edwards et al. |
| 5,833,621 | A | 11/1998 | Panescu et al. |
| 5,842,473 | A | 12/1998 | Fenster et al. |
| 5,919,137 | A | 7/1999 | Finger et al. |
| 5,964,707 | A | 10/1999 | Fenster et al. |
| 5,993,390 | A | 11/1999 | Savord et al. |
| 6,019,725 | A | 2/2000 | Vesely et al. |
| 6,063,032 | A | 5/2000 | Grunwald |
| 6,101,409 | A | 8/2000 | Swanson et al. |
| 6,135,960 | A | 10/2000 | Holmberg |
| 6,176,829 | B1 | 1/2001 | Vilkomerson |
| 6,248,073 | B1 | 6/2001 | Gilbert et al. |
| 6,379,304 | B1 | 4/2002 | Gilbert et al. |
| 6,461,298 | B1 | 10/2002 | Fenster et al. |
| 6,482,161 | B1 | 11/2002 | Sumanaweera et al. |
| 6,490,474 | B1 | 12/2002 | Willis et al. |
| 6,526,163 | B1 | 2/2003 | Halmann et al. |
| 6,544,175 | B1 | 4/2003 | Newman |
| 2003/0036696 | A1 | 2/2003 | Hurd et al. |

OTHER PUBLICATIONS

Christine Merdes, et al "Locating a Catheter Transducer in a Three–Dimensional Ultrasound Imaging Field" IEEE Transaction on Biomedical Engineering, V. 48, No. 12, pp. 1444–1452, Dec. 2001.

Ivan Salgo, et al "Going 'live' with 3–D Cardiac Ultrasound" Focus on Imaging, Special in Today in Cardiology.

Christine Merdes, et al "A Method for Locating a Catheter Transducer in a 3–D Ultrasound Field" Proceedings of the first joint BMES/EMBS Conference Serving Humanity, Advancing Technology, Oct. 13–16, 1999.

PCT International Search Report for PCT/US04/010896, Applicant: Scimed Life Systems, Inc., Forms PCT/ISA/210 and 220, dated Aug. 18, 2004 (7 pages).

PCT Written Opinion of the International Search Authority for PCT/US04/010896, Applicant: Scimed Life Systems, Inc., Form PCT/ISA/237, dated Aug. 18, 2004 (7 pages).

|  | RECEIVE | | | | | | | | | | |
|---|---|---|---|---|---|---|---|---|---|---|---|
| TRANSMIT | | TXVR1 | TXVR2 | TXVR3 | TXVR4 | TXVR5 | TXVR6 | TXVR7 | TXVR8 | RX1 | RX2 | RX3 |
| | TXVR1 | X | d1 | d2 | d3 | d4 | d5 | d6 | d7 | d8 | d9 | d10 |
| | TXVR2 | d11 | X | d12 | d13 | d14 | d15 | d16 | d17 | d18 | d19 | d20 |
| | TXVR3 | d21 | d22 | X | d23 | d24 | d25 | d26 | d27 | d28 | d29 | d30 |
| | TXVR4 | d31 | d32 | d33 | X | d34 | d35 | d36 | d37 | d38 | d39 | d40 |
| | TXVR5 | d41 | d42 | d43 | d44 | X | d45 | d46 | d47 | d48 | d49 | d50 |
| | TXVR6 | d51 | d52 | d53 | d54 | d55 | X | d56 | d57 | d58 | d59 | d60 |
| | TXVR7 | d61 | d62 | d63 | d64 | d65 | d66 | X | d67 | d68 | d69 | d70 |
| | TXVR8 | d71 | d72 | d73 | d74 | d75 | d76 | d77 | X | d78 | d79 | d80 |

METHOD AND SYSTEM FOR REGISTERING ULTRASOUND IMAGE IN THREE-DIMENSIONAL COORDINATE SYSTEM

FIELD OF THE INVENTION

The present inventions generally relate to medical imaging systems and methods, and more particularly to systems and methods for registering ultrasound images in a coordinate system.

BACKGROUND OF THE INVENTION

For purposes of diagnosis and treatment planning, imaging techniques are commonly used in medical procedures to view the internal anatomy of a patient's body. Although the technology for rendering real-time 3-D ultrasound images of most internal organs have been around for several years, real-time 3-D ultrasound in cardiology requires much higher frame rates for real-time acquisition and display to keep up with the beating heart or other cardiac motions. Until recently, 3-D rendered images of the heart have been generating on a non-real-time basis by sequentially acquiring two-dimensional and then using a workstation to input these images for volume rendering.

Recent advancements in transducer and processing technology have enabled commercially available real-time 3-D ultrasound imaging of the heart and surrounding vasculature. For example, the SONOS 7500 imaging system, marketed by Philips Medical System located in Bothell, Wash., is an example of one such commercially available system that uses an external device to generate the image. This system provides real-time 3-D images of cardiac structures with resolution that is adequate for assisting in catheter navigation and placement during electrophysiology procedures. See, e.g., Lang et al., "A Fantastic Journey: 3D Cardiac Ultrasound Goes Live," Radiology Management, November/December 2002; and "Phillips Prepares to Launch System Upgrade Capable of True Real-Time 3D Echo," Diagnostic Imaging Scan, The Global Biweekly of Medical Imaging, Vol. 16, No. 18, Sep. 11, 2002, the disclosures of which are hereby expressly incorporated herein by reference.

During electrophysiological therapy, ablation is used to treat cardiac rhythm disturbances. During these procedures, a physician steers a catheter through a main vein or artery into the interior region of the heart that is to be treated. The physician places an ablating element carried on the catheter near the targeted cardiac tissue that is to be ablated, and directs energy from the ablating element to ablate the tissue and form a lesion. Such a procedure may be used to treat arrhythmia, a condition in the heart in which abnormal electrical signals are generated in the heart tissue.

To some degree, a real-time 3-D imaging system, such as the SONOS 7500, obviates the need for a 3-D catheter navigation system. A 3-D navigation system, however, would still be very useful for correlation of catheter position and internal anatomical structures with previously recorded signals and ablation locations.

In one navigation system, commercially available as the Realtime Position Management™ (RPM) tracking system developed by Boston Scientific Corporation, located in San Jose, Calif. a graphical representation of a catheter is displayed in a 3-D computer-generated representation of a body tissue, e.g., heart chamber. The 3-D representation of the body tissue is produced by mapping the geometry of the inner surface of the body tissue in a 3-D coordinate system by placing plurality of ultrasound positioning transducers on a catheter, and moving the catheter to multiple points on the body tissue while tracking the positions of the catheter within the global coordinate system using the positioning transducers. A graphical anatomical shell is then deformed to conform to the transducer positions as they are acquired. The positions of other catheters to be guided within the body, e.g., a mapping/ablation catheter, is determined by placing ultrasound transducers on the these catheters and tracking the positions of the catheters within the 3-D coordinate system.

In the case of cardiac treatment, electrical activity sensed by the ablation/mapping catheter can be correlated with the sensed positions of the catheter in order to generate and register an electrophysiology map within the 3-D coordinate system. Tissue associated with abnormal activity, such as cardiac arrhythmia, can then be treated by guiding the ablation electrode of the mapping/ablation catheter into contact with the tissue, as shown on the electrophysiology map, and energizing the electrode to create a lesion on the tissue.

Recent work at Duke University has demonstrated the ability to localize catheters within a 3-D ultrasound image, such as that generated by the SONOS 7500 imaging system. See, e.g., Merdes et al., "Locating a Catheter Transducer in a Three-Dimensional Ultrasound Imaging Field," IEEE Transactions on Biomedical Engineering, Vol. 48, No. 12, December 2001, pages 1444–52, which is expressly incorporated herein by reference. This method involves determining the location of an ultrasound transducer, which is to be carried by a catheter to be tracked, within the coordinate system of the 3-D image. The main limitation of this method is that, because it reports the location of the transducer within the coordinate system of the 3-D image, the coordinate system will change as the position of the imaging device changes, and thus, any previously registered mapping data and ablation locations will be lost. This becomes even more crucial if the imaging device is an internal device, e.g., a intracardiac or transesophogeal imaging probe, which is often maneuvered within the body of the patient during the imaging process.

There thus remains a need for an improved system and method for localizing an image within the body of a patient.

SUMMARY OF THE INVENTION

The present inventions are directed to methods and systems for imaging internal anatomical structures. The internal anatomical structure can be tissue found inside the body of a patient. For example, the internal anatomical structure can be an internal organ, such as a heart. In the inventive method and system, ultrasound image data of the internal anatomical structure is acquired and arranged in a first coordinate system. The ultrasound image data can either be acquired internally (e.g., by using an internal peripheral device, such an intracardiac imaging probe or a transesophogeal imaging probe) or externally (e.g., by using an external peripheral device).

The location of at least one ultrasound transducer is determined within this first coordinate system and a second coordinate system (e.g., using a registration subsystem having one or more processors). Although not necessary, the second coordinate system is preferably fixed relative to the internal anatomical structure (e.g., by establishing the second coordinate system within the internal anatomical structure itself), so that the second coordinate system need not be modified if the internal anatomical structure moves.

The first and second coordinate systems can be variously configured. For example, the first coordinate system can be a local three-dimensional coordinate system, and specifically a spherical coordinate system, and the second coordinate system can be a global three-dimensional coordinate system, and specifically a Cartesian coordinate system. Other types of coordinate systems can be envisioned as well. The second coordinate system can be a spherical coordinate system, and the first coordinate system a Cartesian coordinate system. Or both the first and second coordinate systems can be Cartesian coordinate systems or both can be spherical coordinate systems.

The location of the ultrasound transducer(s) within the first coordinate system can be determined in a variety of ways. For example, ultrasound signals can be generated between the ultrasound transducer(s) and one or more other ultrasound transducers fixed relative to a location at which the ultrasound image data is acquired. In this case, the locations of the ultrasound transducer(s) within the first coordinate system can be at least partially based on one or more measured characteristics (e.g., amplitudes and/or transit times) of the received ultrasound signals. Preferably, the other ultrasound transducer(s) have dual functionality in that they are used to acquire at least a portion of the ultrasound image data in additional to locating the ultrasound transducer(s). The location of the ultrasound transducer(s) within the second coordinate system can also be determined in a variety of ways. For example, ultrasound signals can be generated between the ultrasound transducer(s) and reference ultrasound transducer(s).

A transformation between the first and second coordinate systems is performed based on the determined location of the ultrasound transducer within the first and second coordinate systems. The first coordinate system can be transformed into the second coordinate system, or vice versa. In the former case, the ultrasound image data can be registered in the second coordinate system (e.g., by an image processor) in accordance with the coordinate system transformation and displayed as an ultrasound image of the internal anatomical structure. Additionally, graphical information (e.g., an anatomical site of interest) can be generated and registered in the second coordinate system (e.g., by a graphical processor), and displayed with the ultrasound image of the internal anatomical structure. If, on the other hand, the second coordinate system is transformed into the first coordinate system, graphical information can be generated in the second coordinate system, and registered within the first coordinate system in accordance with the coordinate system transformation and displayed with the image data, which would be registered within the first coordinate system in a standard manner.

Although the present inventions should not be so limited in its broadest aspects, the transformation of the two coordinate systems allows image data and graphical data (e.g., an ablation site or electrophysiology site) originally registered in the respective first and second coordinate system to be properly displayed with one another regardless of whether the imaging device that acquires the image data moves. This is because the second coordinate system is not tied to the imaging device.

In one specific implementation of imaging the internal anatomical structure, a plurality of ultrasound beams are transmitted along a respective plurality of scan lines that intersect the anatomical structure. Ultrasound image data is then acquired from the portion of the ultrasound beams reflected from the internal anatomical structure. One or more characteristics (e.g., an amplitude and/or transit time) of each of the ultrasound beams is then measured with an ultrasound positioning transducer. A location of the positioning transducer within the first coordinate system is then determined based on the measured characteristic(s). This can be accomplished in any of a variety of manners.

For example, in the case of a spherical coordinate system, the radial coordinate of the positioning transducer can be determined by first determining which scan line intersects the positioning transducer based on the amplitude of the ultrasound beam corresponding to that scan line. In the preferred embodiment, the scan line that corresponds with the ultrasound beam having the greatest measured amplitude is selected as the intersecting scan line. The length of the intersecting scan line between its origin and the positioning transducer is then determined by measuring the transit time of the corresponding ultrasound beam. A radial coordinate, equal to the length of the intersecting scan line. The angular coordinates, and specifically the azimuthal and elevational coordinates, of the positioning transducer can be determined by assigning the angular coordinates of the intersecting scan line to the positioning transducers. Alternatively, the azimuthal and elevational coordinates of the positioning transducer can be determined by comparing measured amplitudes of the ultrasound beams to simulated unique receive profiles within a look-up matrix, and assigning the angular coordinates associated within the receive profile having the greatest correlation value to the positioning transducer.

Once the location of the positioning transducer within the respective first and second coordinates systems is known, the location of the positioning transducer within the second coordinate system is then determined, and the coordinate system transformation is then performed, as previously described. Preferably, at least three positioning transducers are used to allow transformation between three-dimensional coordinate systems.

Other objects and features of the present invention will become apparent from consideration of the following description taken in conjunction with the accompanying drawings.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE PREFERRED EMBODIMENTS

Figure 1:
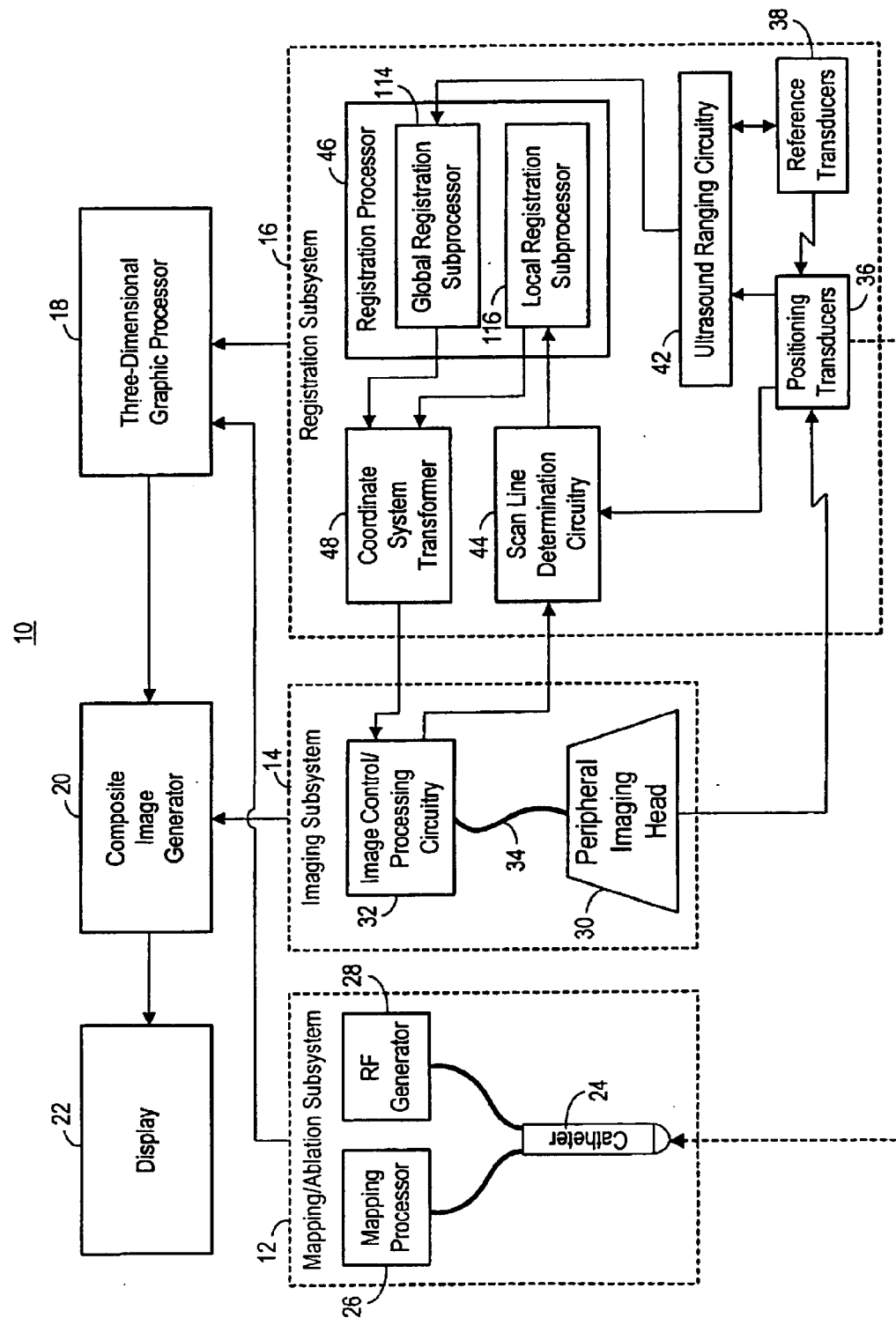
FIG. 1 is a functional block diagram of one preferred embodiment of a medical treatment system constructed in accordance with the present inventions.

Referring to FIG. 1, an exemplary medical treatment system 10 constructed in accordance with the present inventions is shown. The treatment system 10 is particularly suited for imaging, mapping, and treating the heart. Nevertheless, it should be appreciated that it can be used for treating other internal anatomical structures, e.g., the prostrate, brain, gall bladder, uterus, esophagus and other regions in the body. The treatment system 10 generally comprises (1) a mapping/ablation subsystem 12 for mapping and ablating tissue within the heart; (2) an imaging subsystem 14 for generating image data of the heart; (3) a registration subsystem 16 for registering the image and mapping data within a 3-D graphical environment; (4) a 3-D graphical processor 18 for generating 3-D graphical data of the environment in which the imaged body tissue is contained; (5) a composite image generator 20 for generating a composite image from the registered image data and 3-D graphical data; and (6) a display 22 for displaying the composite image. It should be noted that the elements illustrated in FIG. 1 are functional in nature, and are not meant to limit the structure that performs these functions in any manner. For example, several of the functional blocks can be embodied in a single device, or one of the functional blocks can be embodied in multiple devices. Also, the functions can be performed in hardware, software, or firmware.

I. Mapping/Ablation Subsystem

Figure 2:
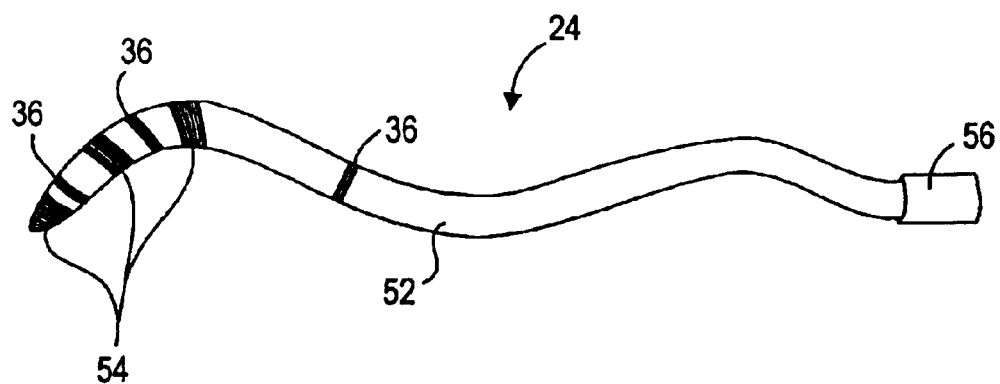
FIG. 2 is a plan view of a mapping/ablation catheter used in the medical treatment system of FIG. 1.

The mapping/ablation subsystem 12 is utilized to identify and treat a target tissue site or sites, e.g., aberrant conductive pathways. To this end, the mapping/ablation subsystem 12 comprises a mapping/ablation catheter 24, a mapping processor 26, and a radio frequency (RF) generator 28. As further illustrated in FIG. 2, the mapping/ablation catheter 24 comprises an elongate catheter member 52, a plurality of electrodes 54 (in this case, three) carried at the distal end of the catheter member 52, and a handle 56 carried at the proximal end of the elongate member 52. All three electrodes 54 on the catheter member 52 are configured to detect electrical signals in the myocardial tissue for subsequent identification of target sites. The electrode 54 at the distal tip of the catheter member 52 is also configured to be used as an ablation electrode to provide ablation energy to the targeted sites when placed adjacent thereto and operated.

The handle 56 includes an electrical connector (not shown) for electrical coupling to the mapping processor 26 and RF generator 28.

Referring back to FIG. 1, the mapping processor 26 is configured to derive activation times and voltage distribution from the electrical signals obtained from the electrodes 54 to determine irregular electrical signals within the heart, which can then be graphically displayed as a map. Mapping of tissue within the heart is well known in the art, and thus for purposes of brevity, the mapping processor 26 will not be described in further detail. Further details regarding electrophysiology mapping are provided in U.S. Pat. Nos. 5,485,849, 5,494,042, 5,833,621, and 6,101,409, which are expressly incorporated herein by reference.

The RF generator 28 is configured to deliver ablation energy to the ablation electrode (i.e., the distal most electrode 54) in a controlled manner in order to ablate sites identified by the mapping processor 26. Alternatively, other types of ablative sources besides the RF generator 28 can be used, e.g., a microwave generator, an ultrasound generator, a cryoablation generator, and a laser or other optical generator. Ablation of tissue within the heart is well known in the art, and thus for purposes of brevity, the RF generator 28 will not be described in further detail. Further details regarding RF generators are provided in U.S. Pat. No. 5,383,874, which is expressly incorporated herein by reference.

It should be noted that other types of mapping/ablation catheters can be used in the treatment system 10. For example, a catheter having a basket structure of resilient splines, each of which carries a plurality of dedicated mapping electrodes can be used. This catheter may be placed in a heart chamber, so that the resilient splines conform to the endocardial surface of the heart, thereby placing and distributing the mapping electrodes along the entire endocardial surface of the cavity for efficient mapping. The catheter may also have a roving ablation electrode that can be steered in contact with the ablation sites identified by the mapping electrodes. Or a separate ablation catheter with a dedicated ablation electrode or electrodes can be used.

II. Imaging Subsystem

The imaging subsystem 14 generally comprises a peripheral imaging device 30, which generates and detects ultrasound signals representing the interior of the body, image control/processing circuitry 32 for processing these signals into image data, and cabling 34 coupling the imaging device 30 to the image control/processing circuitry 32. In the illustrated embodiment, the peripheral imaging device 30 is an external device configured to be placed on the skin of a patient for imaging of internal organs. For example, it can be placed on the patient's chest in order to image the heart. It should be noted, however, that an internal imaging device, e.g., an intracardiac imaging catheter or transesophogeal imaging probe can also be used to image the heart.

Figure 3:
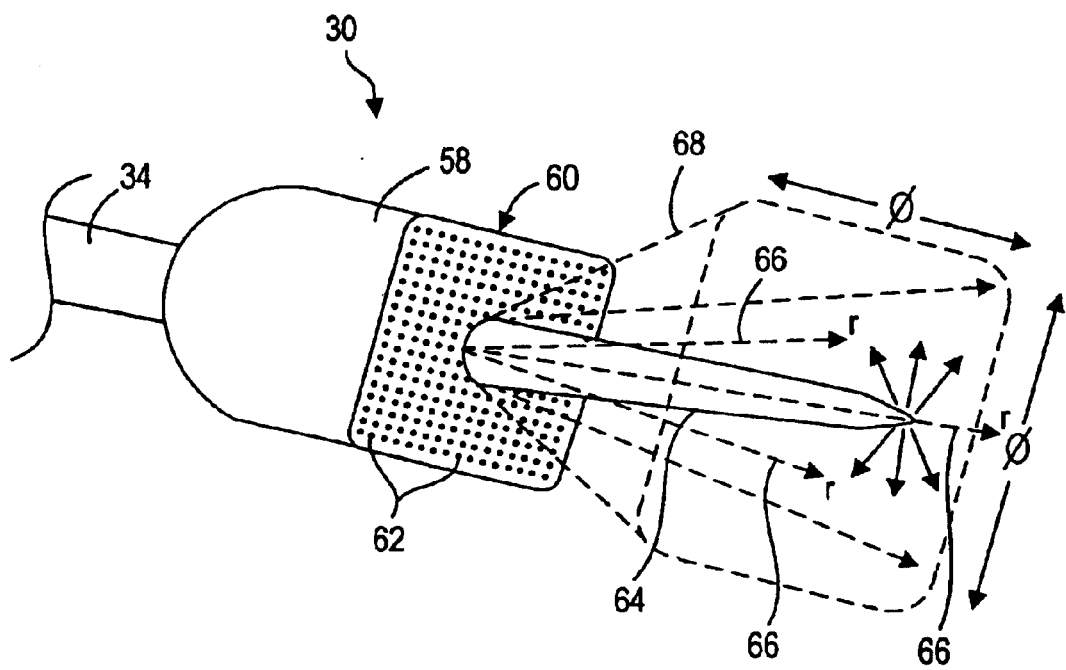
FIG. 3 is a perspective view of a peripheral imaging head that can be used in the imaging subsystem illustrated in FIG. 1.

Referring now to FIG. 3, the peripheral imaging device 30 comprises an imaging head 58 carrying a transducer array 60 of ultrasound imaging transducers 62 that are capable of steering a far-field ultrasound beam 64 along scan lines 66 within a pyramidal volume 68. In the illustrated embodiment, the ultrasound transducer array 60 is arranged in a 16×16 transducer matrix that transmits 256 scan lines 66 (only three shown) with a 4 degree separation of lines. In this case, the scanned pyramidal volume will cover an angular range of 64 degrees in the azimuth and elevation. Thus, it can be appreciated that the ultrasound transducer array 60 acquires ultrasound image data that is arranged in a spherical coordinate system defined by angular coordinates in the azimuth ($\theta$) and elevation ($\phi$), and a radial coordinate (r).

It should be noted that the number of transducers 62 in the array 60 can be increased in order to increase the resolution and/or angular range of the imaging head 58. For example, the transducer array of the commercially available SONOS 7500 imaging system comprises thousands of transducers that provide a resolution sufficient to image the detailed structures of the heart, e.g., the valves, in real time.

Figure 4:
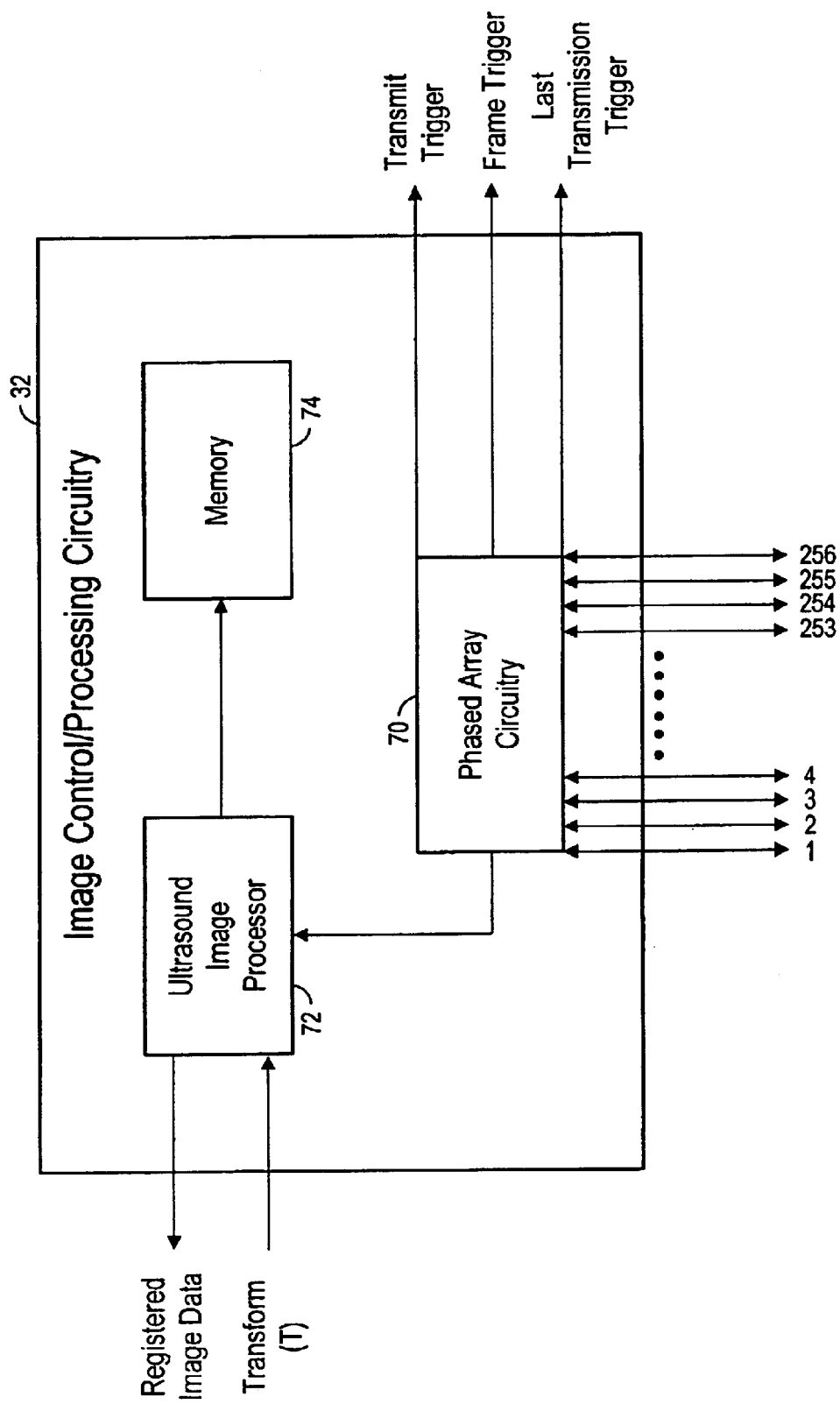
FIG. 4 is a functional block diagram of one preferred implementation of the image control/processing circuitry illustrated in FIG. 1.

Referring to FIG. 4, the image control/processing circuitry 32 includes phased array control circuitry 70 coupled to the transducer array 60 via signal wires (not shown) extending through the cable 34. Using conventional methods, the phased array control circuitry 70 steers the ultrasound beam 64 along the defined scan lines 66 in order to acquire ultrasound image data from tissue intersected by these scan lines 66. The image control/processing circuitry 32 further includes an ultrasound image processor 72 coupled to the phased array control circuitry 70 for processing the ultrasound image data, and specifically, for transforming the image data from the local imaging coordinate system (i.e., the spherical coordinate system) into the global coordinate system based on the input of a transform calculated by the registration subsystem 16, as will be described in further detail below. The image control/processing circuitry 32 also includes memory 74 for storing the transformed image data for eventual output to the composite image generator 20.

To obtain an ultrasound image of the heart, the imaging head 58 of the peripheral imaging device is placed on the skin surface of the body, and specifically the chest area, with the ultrasound transducer array 60 facing the heart. The image control/processing circuitry 32 is then operated to transmit electrical pulses to the respective imaging transducers 62 of the array 60 in a defined sequence, amplitude, and phase, such that the ultrasound beam scans the pyramidal volume 64 along the scan lines 66. The image control/processing circuitry 32 also receives and processes reciprocal electrical pulses (representing image data) from the array 60.

Thus, to generate an image frame, the phased array circuitry 70 transmits electrical signals through the signal wires to the transducer array 60 in the defined sequence, amplitudes, and phases. The transducer array 60 converts the electrical pulses into ultrasound energy as an ultrasound beam 64 that is emitted into the heart along the first scan line 66. A portion of the ultrasound energy is reflected off of the heart back to transducer array 60. The transducer array 60 converts the back-reflected ultrasound energy into electrical signals representing the portion of the heart intersected by the first scan line 66, which is transmitted back through the signal wires to the phased array circuitry 66. The electrical signals are detected by the phased array circuitry 70 and outputted to the ultrasound image processor 72, which stores it as an ultrasound image data point. This process is sequentially repeated for the remaining scan lines 66 in order to acquire and store data points for the entire frame, i.e., 256 data points.

Using standard transformation techniques, the imaging processor 72 will then transform the imaging data from a spherical coordinate system $(r, \theta, \phi)$ into a Cartesian coordinate system $(x', y', z')$, which is then stored in memory 74. Once the imaging processor 72 obtains the transform T from the registration subsystem 16, as will be described in further detail below, it will then recall the image data from memory 74, and transform the image data from the local Cartesian coordinate system $(x', y', z')$ into the global Cartesian coordinate system $(x, y, z)$ established by the registration subsystem 16.

The phased array circuitry 70 generates timing signals, and specifically a transmission trigger that indicates the start time of each beam transmission, a last transmission trigger that indicates the last beam transmission of the imaging cycle, and a frame trigger that indicates the end of each imaging cycle. Notably, a dead period is created at the end of each imaging cycle, in which case, the start time of the last beam transmission and the end time of the respective imaging cycle will not be coincident with each other. The use of these timing signals and the dead period will be described in further detail below.

III. Registration Subsystem

Referring back to FIG. 1, the registration subsystem 16 generally comprises (1) a plurality of ultrasound transducers, and specifically, ultrasound positioning transducers 36 and ultrasound reference transducers 38; (2) ultrasound ranging circuitry 42 configured for determining distances between various combinations of the ultrasound transducers 36 and 38 in the form of time data; (3) scan line processing circuitry 44 configured for determining the peak amplitudes and transit times of the imaging signals transmitted between the transducer array 60 and the positioning transducers 36; (4) a registration processor 46 configured for registering the positioning transducers 36 within the global coordinate system based on the time information provided by the ultrasound ranging circuitry 42, and for registering the positioning transducers 36 within the local imaging coordinate system based on the amplitude and transmit time data provided by the scan line processing circuitry 44; and (5) a coordinate system transformer 48 configured for transforming the local imaging coordinate system into the global coordinate system.

A. Ranging Transducers

In the illustrated embodiment, the ultrasound reference transducers 38 are mounted on a pair of reference catheters (not shown). For example, the number of reference transducers 38 can total eight, with four reference transducers 38 mounted on each reference catheter. The reference catheters can be placed anywhere within the body (preferably, a known location) that arranges the reference transducers 38 in 3-D space, and that allows the reference transducers 38 to communicate with the positioning transducers 36. For example, the first two dimensions of the coordinate system are provided by placing one of the reference catheters within the coronary sinus (CS) of the heart to arrange its four reference transducers 38 in a two-dimensional plane, and the third dimension is provided by placing by placing the other reference catheter within the right ventricular (RV) apex of the heart to arrange its four reference transducers 38 off of the two-dimensional plane. It should be noted that only three of the reference transducers 38 located on the CS reference catheter are needed to provide the first two dimensions of the coordinate system, while only one of the reference transducers 38 located on the RV reference catheter is needed to provide the third dimension. The remaining reference transducers 38 are redundant and are used to improve the accuracy of the triangulation process.

The positioning transducers 36 are mounted at the distal end of a mapping/ablation catheter 24 (shown in FIG. 2), one of which is mounted at the distal tip just proximal to the tip electrode 32, and the remaining two of which are mounted proximally on the distal end. The positioning transducers 36 facilitate the mapping of electrophysiological information within the heart chamber and the subsequent ablation thereof. As will be described in further detail below, the positioning transducers 36 also facilitate structural mapping of the endocardial surface of the heart chamber as the mapping/ablation catheter 24 is moved around within the chamber. Optionally, or alternatively, a positioning transducer 36 can be mounted on the distal tip of a separate marking catheter (not shown) to provide a dedicated means for structurally mapping the heart. Further details on the use of ultrasound transducers within the heart are described in U.S. Pat. No. 6,490,474 and U.S. patent application Ser. No. 09/128,304, entitled "A dynamically alterable three-dimensional graphical model of a body region," which are fully and expressly incorporated herein by reference.

B. Ranging Circuitry

The ultrasound ranging circuitry 42 is configured for conditioning the positioning transducers 36 as receivers, i.e., to receive ultrasound pulses, and for conditioning the ultrasound reference transducers 38 as transceivers, i.e., to both transmit and receive ultrasound pulses. As can be appreciated, ultrasound transducers can be operated as transmitters by stimulating them with electrical pulses, which in turn causes the transducers to vibrate and transmit ultrasound pulses. Ultrasound transducers can be operated as receivers by receiving electrical pulses that are induced by the receipt of ultrasound pulses and subsequent vibration of the transducers.

The ultrasound ranging circuitry 42 is configured for determining the distances between the reference transducers 38 by conditioning each reference transducer 38 to transmit an electrical pulse, and the conditioning the remaining reference transducers 38 to receive that electrical pulse. The ultrasound ranging circuitry then measures the "time-of-flight" for each ultrasound signal. As will be described in further detail below, the registration processor 46 will calculate distances from this time information, which can then be triangulated in order to establish a global coordinate system.

The ultrasound ranging circuitry 42 is also configured for determining the distances between the reference transducers 38 and the positioning transducers 36 by conditioning each of the reference transducers 38 to transit an ultrasound pulse, and conditioning the positioning transducers 36 to receive this ultrasound pulse. The ultrasound ranging circuitry then measures the "time-of-flight," i.e., the transit time, for each ultrasound signal. As will be described in further detail below, the registration processor 46 will calculate distances from this time information, which can then be triangulated in order to determine the positions (x, y, z) of the positioning transducers 36, and thus any structure or tissue adjacent the positioning transducers 36, within the established global coordinate system.

Figures 5, 9:
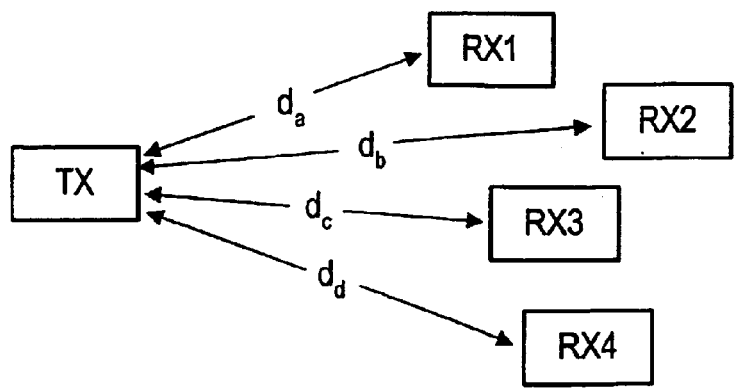
FIG. 5 is a table illustrating a distance matrix formed by calculating the distances between the positioning and reference transducers illustrated in FIG. 1.
FIG. 9 is a functional block diagram of a positional arrangement between a plurality of ultrasound receiving transducers and an ultrasound transmitting transducer.

Thus, it can be seen from FIG. 5 that an eight-by-eleven distance matrix, which is defined by the eight transmitting transducers on one side (eight reference transducers 38 (TXVR1–8) and eleven receiving transducers on the other side (eight reference transducers 38 (TXVR1–8) and three positioning transducers 36 (RX1–3) located on the mapping catheter), is formed. This matrix contains the transit time of the ultrasound pulses transmitted between each transmitting transducer and the respective receiving transducers. As will be described in further detail below, the distances (d1–80) between the respective transducers can then be calculated using these transit time values.

Figure 6:
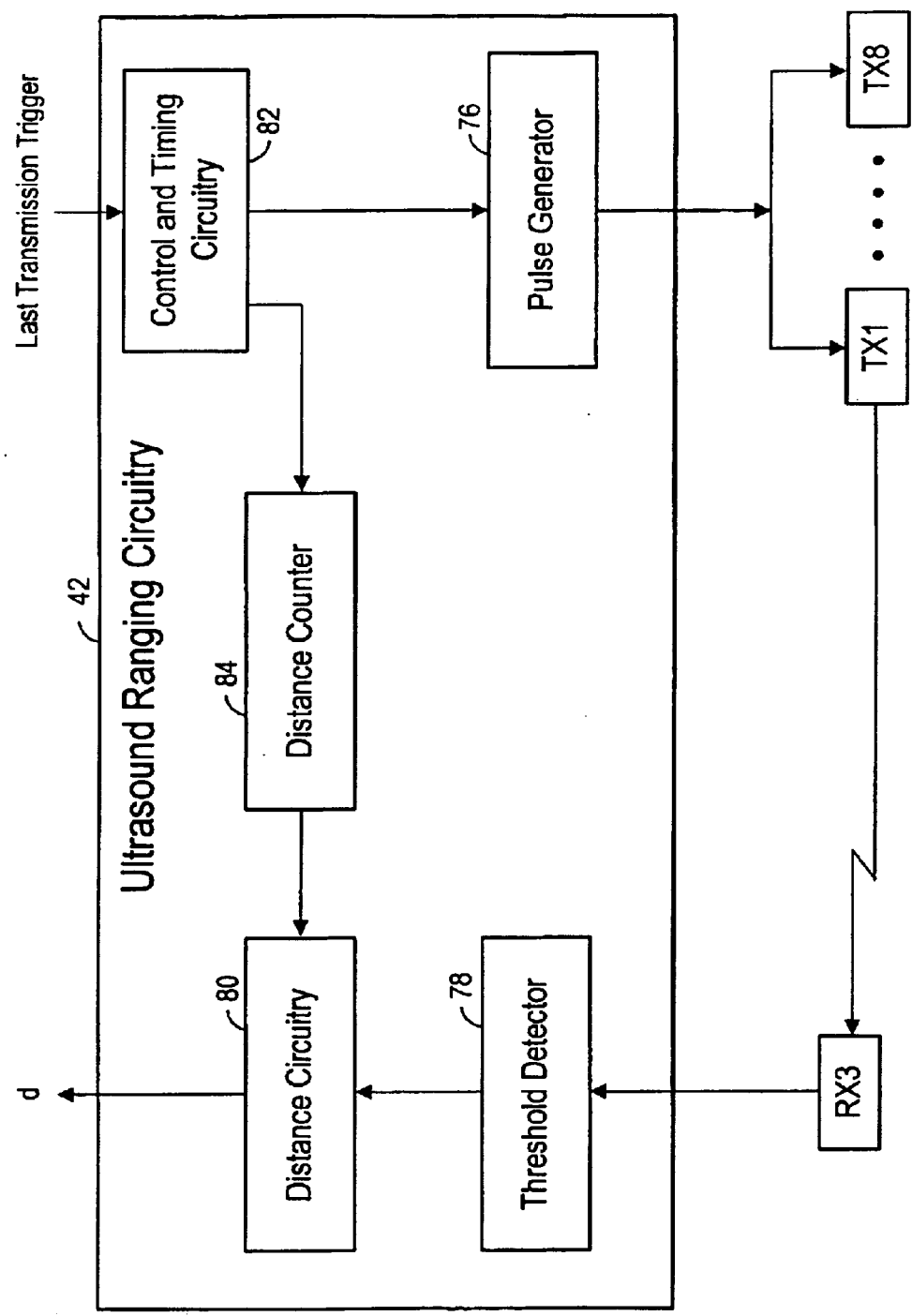
FIG. 6 is a functional block diagram of one preferred implementation of the ultrasound ranging circuitry illustrated in FIG. 1.

Turning now to FIG. 6, the components of the ranging circuitry 42 will now be described in further detail. For purposes of simplicity, the components of the ranging circuitry 42 are described in the context of determining distances between a single receiving transducer RX (e.g., one of the positioning or reference transducers 36/38) and multiple transmitting transducers TX1–8, (e.g., the reference transducers 38). It should be appreciated, however, that the ranging circuitry 42 illustrated in FIG. 6 can be readily modified to determine of the distances provided in FIG. 5 amongst all of the positioning and reference transducers 36 and 38.

The ranging circuitry 42 includes a pulse generator 76 coupled to the transmitting transducers TX1–8, a threshold detector 78 coupled to the receive transducer RX, distance circuitry 80 coupled to the threshold detector 78, control and timing circuitry 82 coupled to the pulse generator 76, and a distance counter 84 coupled to the control and timing circuitry 82. The pulse generator 76 is configured for generating electrical pulses that are transmitted to the transmitting transducers TX 1–8, which convert the electrical pulses into ultrasound pulses. The control and timing circuitry 82 operates the pulse generator 76, such that the pulses are generated at the desired frequency and spacing. In the illustrated embodiment, the electrical pulses are single cycle 500 KHz pulses that are transmitted at a rate of one pulse per millisecond. The control and timing circuitry 82 also controls the multiplexing between the pulse generator 76 and the transmitting transducers TX1–8, such that the transmitting transducers TX1–8 are stimulated by the electrical pulses in a sequential fashion. Thus, the control and timing circuitry 82 will cause the first transducer TX1 to transmit an ultrasound pulse, then the second transducer TX2, and so on until the last reference transducer TX8 transmits an ultrasound pulse. The control and timing circuitry 82 will then cycle through the transmitting transducers TX1–8 again.

Coincident with the transmission of each ultrasound pulse from a transmitting transducer TX, the control and timing circuitry 82 is configured for triggering the distance counter 84 to begin counting from zero. The running count value of the distance counter 84 provides a measure of time from the transmission of the ultrasound pulse. This distance counter 84 is reset to zero upon the transmission of the next ultrasound pulse.

After each ultrasound pulse has been transmitted, the receive transducer RX receives the ultrasound pulse and converts the ultrasound pulse into an electrical pulse. The threshold detector 78 is configured for detecting the electrical pulse that is above a threshold level, e.g., a voltage level. The distance circuitry 80 listens for the transmitted pulse within a time window, e.g., 100 $\mu$sec. The time window may begin immediately or shortly after the transmitted pulse has been transmitted. In determining the time of detection of the transmitted pulse by each receiving transducer, the distance circuitry 80 interprets the first signal that the threshold detector 78 detects within the time window as the received pulse. Upon receipt of a detected electrical pulse from the threshold detector 78, the distance circuitry 80 reads the current count from the distance counter 84, which provides a distance measurement between the receive transducer RX and the current transmitting transducer TX in the form of an elapsed time between the transmission of the transmit pulse and the detection of the receive pulse.

As will be described in further detail below, the registration subsystem 16 uses the positioning transducers 36 to receive ultrasound imaging pulses from the transducer array 60 in order to determine the distances between the transducer array 60 and the positioning transducers 36, as well as the scan lines 66 that intersect the positioning transducers 36. In order to prevent interference between this function, the registration subsystem 16 time multiplexes the receipt of the imaging ultrasound pulses from the transducer array 60 and the positioning ultrasound pulses from the reference transducers 38.

To this end, the previously described dead period is placed at the end of the imaging cycle to provide the positioning transducers 36 with a separate reception period. Thus, the ranging circuitry 42 only transmits and receives ultrasound pulses between the transmitting transducers TX 1–8 and receiving transducer RX during this dead period. The ranging circuitry 42, and in particular, the control and timing circuitry 82, is coupled to the phased array circuitry 70 of the imaging control/processing circuitry 32 in order to obtain the last transmission trigger, indicating the end of the imaging beam transmission within the cycle, and thus the beginning of the dead period during which the ranging circuitry 42 can obtaining ranging data. In the illustrated embodiment, the imaging cycle has a duration of 53 milliseconds, 45 milliseconds of which is dedicated to the imaging function, and 8 seconds of which is dedicated to the ranging function.

C. Scan Line Processing Circuitry

Figure 7:
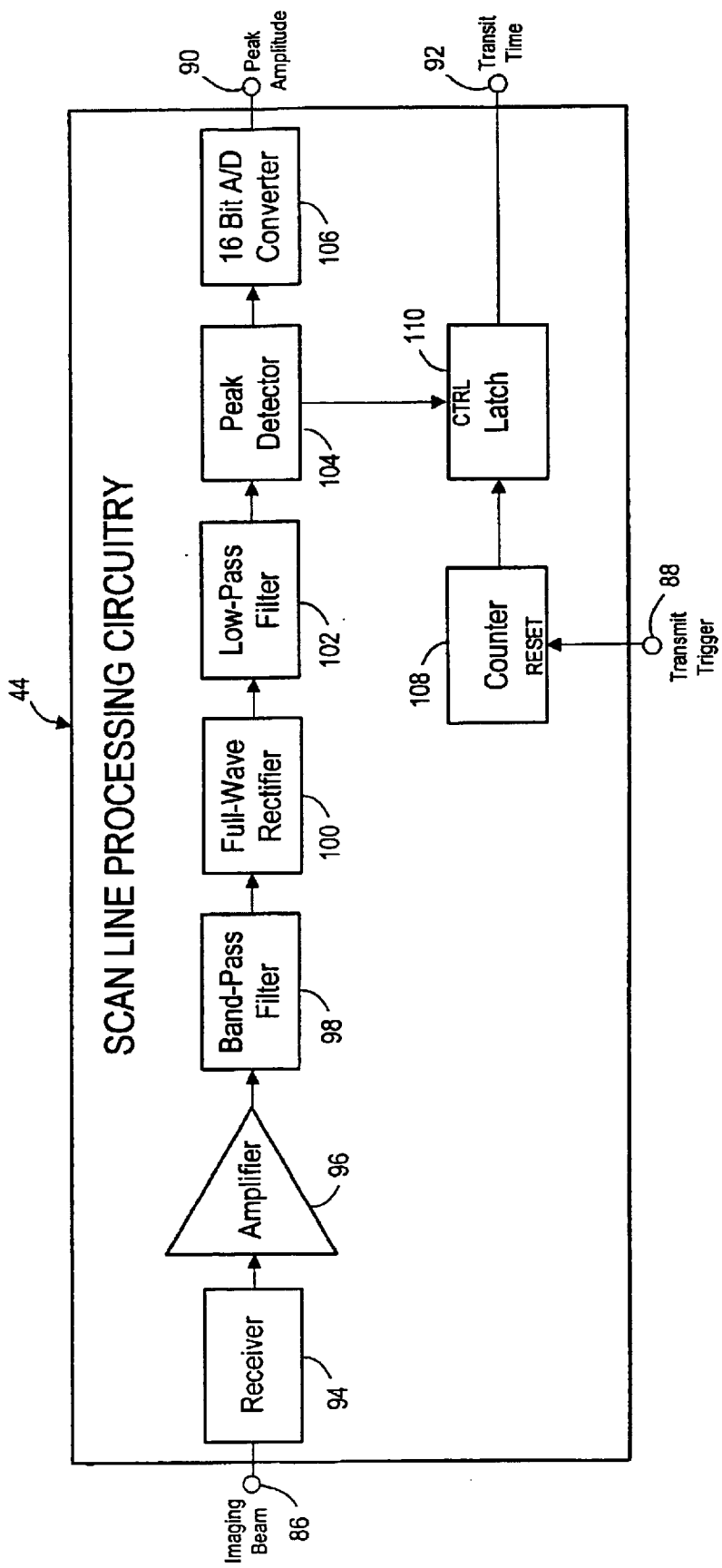
FIG. 7 is a functional block diagram of one preferred implementation of the scan line determination circuitry illustrated in FIG. 1.

Turning now to FIG. 7, the components of the scan line processing circuitry 44 will now be described in further detail. For purposes of simplicity, the components of the scan line processing circuitry 44 are described in the context of a single positioning transducer 36. It should be appreciated, however, that the scan line processing circuitry 44 illustrated in FIG. 7 can be readily modified to provide the same functionality for the remaining positioning transducers 36.

The scan line processing circuitry 44 comprises (1) a scan line input 86 for acquiring signals received by the position transducer 36 (and specifically energy from the imaging beams 64); (2) a transmit trigger input 90 for acquiring the transmission trigger from the image control/processing circuitry 32 indicating each time an ultrasound beam 64 is generated (256 times per imaging cycle); (3) a peak signal output 92 for outputting the peak amplitudes of the imaging beam signals received by the positioning transducer 36; and (4) a transit time output 94 for outputting the transit time of the imaging beams 64 between the phase array 60 and the positioning transducer 36.

At the scan line input 86, the scan line processing circuitry 44 comprises a receiver 94 for receiving the scan line signal (i.e., the imaging beam signal transmitted along a respective scan line), an amplifier 96 for amplifying the imaging beam signal, and a bandpass filter 98 (and specifically a 2.5 MHz bandpass filter) for outputting a substantially noise-free signal. The processing circuitry 44 further comprises a rectifier 100 for outputting the absolute value of the imaging beam signal components, so that the negative portion of the signals, which may contain the majority of the energy, can be later detected. The processing circuitry 44 further comprises a low pass filter 102 for outputting a low frequency signals correlated to the magnitudes of the imaging beam signals, and a peak detector 104 for sensing the peaks of these low frequency signal and outputting analog signals, the amplitudes of which are proportional to the peak amplitudes of the imaging beams 64. Notably, the low pass filter 102 simplifies and makes the peak detector 104 more accurate, which may otherwise be difficult to accomplish with high frequency signals. The processing circuitry 44 further comprises an A/D converter 106 for converting the analog signals from the peak detector 104 into digital signals from 1 to 256 representing the peak amplitudes of the respective imaging beams 64 received by the positioning transducer 36. This digital amplitude data is output to the peak signal output 94 for processing off-line, as will be described in further detail below.

At the transmit trigger input 88, the scan line processing circuitry 44 further comprises a counter 110 that is reset to begin counting from zero in response to the receipt of the transmission trigger on the trigger input 90. That is, the counter 110 will count from zero each time an imaging beam 64 is transmitted from the transducer array 60. Thus, the running count value of the counter 110 provides a measure of time from the transmission of the respective imaging beam 64. This counter 110 is reset to zero upon the transmission of the next imaging beam 64, i.e., upon receipt of the next transmission trigger on the trigger input 90.

The processing circuitry 44 further comprises a latch 112 coupled to the output of the counter 110 for receiving the count value. The latch 112 is also coupled to the peak detector 104 for receiving a signal indicating when the peak of the scan line pulse has been received. Upon receipt of this signal, the latch 112 outputs the count to the transmit time output 94, thereby providing a distance measurement between the transducer array 60 and the positioning transducer 36 in the form of an elapsed time between the transmission and detection of the imaging beam 64. This count will be matched with the respective peak amplitude of the imaging beam 64 placed on the peak amplitude output 92, as will be described in further detail below.

Figure 8:
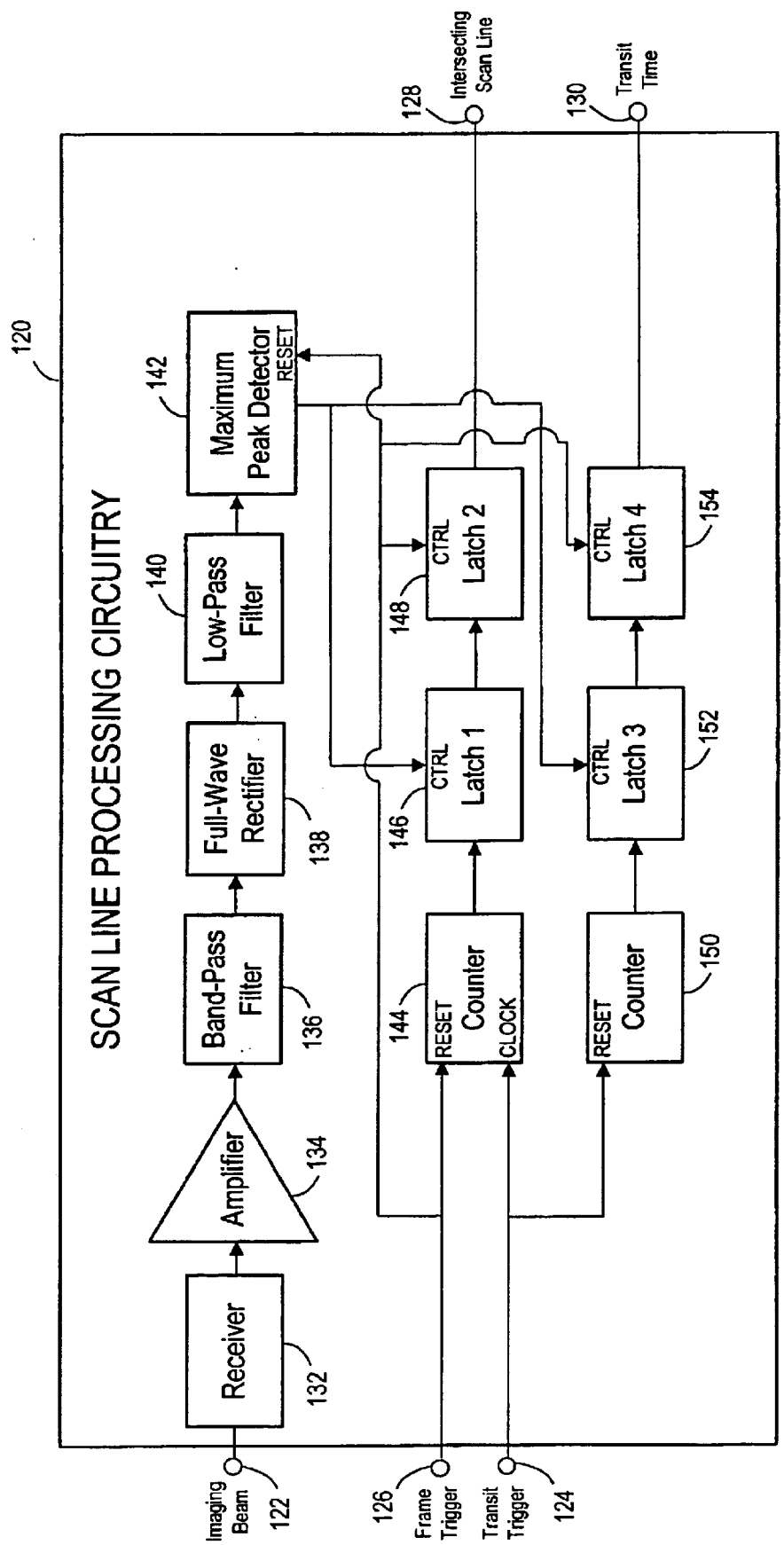
FIG. 8 is a functional block diagram of an alternative preferred implementation of the scan line determination circuitry illustrated in FIG. 1.

Referring now to FIG. 8, an alternative embodiment of scan line processing circuitry 120 is described. The scan line processing circuitry 120 differs from the previously scan line processing circuitry 44 in that it determines the scan line 66 that intersects the positioning transducer 36 and the corresponding transmit time, thereby obviating the need to accomplish this task within the registration processor 46.

To this end, the scan line processing circuitry 120 comprises (1) a scan line input 122 for acquiring signals received by the position transducer 36 (and specifically energy from the imaging beams 64); (2) a transmit trigger input 124 for acquiring the transmission trigger from the image control/processing circuitry 32 indicating each time an imaging beam 64 is generated (256 times per imaging cycle); (3) a frame trigger input 126 for acquiring the frame trigger from the image control/processing circuitry 32 indicating the end of the current frame or imaging cycle; (4) an intersecting scan line output 128 for outputting a signal representing the scan line 66 that intersects the respective positioning transducer 36; and (5) a transit time output 130 for outputting the transit time of the imaging beam 64 transmitted between the phase array 60 and the positioning transducer 36 along the intersecting scan line 66.

At the scan line input 122, the scan line processing circuitry 120 comprises a receiver 132, an amplifier 134, a bandpass filter 136, a rectifier 138, and a low pass filter 140 that are configured to perform the functions previously described with respect to the same named components above. Instead of having a standard peak detector and A/D converter, the processing circuitry 120 comprises a maximum peak detector 142.

The maximum peak detector 142, until reset, will store the maximum peak of the lower frequency signals received from the low pass filter 140, i.e., it will only store the peak amplitude of a lower frequency signal correlated to the current imaging beam 64 if it is greater than the previously stored peak amplitude. The maximum peak detector 142 will output a signal (e.g., high) if the peak amplitude of the current signal is greater than the currently stored maximum peak amplitude. The frame trigger input 126 is coupled to the reset of the maximum peak detector 142, so that it is reset to "0" once the transducer array 60 completes a full imaging cycle.

The processing circuitry 120 comprises a counter 144, the clock input of which is coupled to the transmit trigger input 124. Thus, the counter 144 will increment by "1" each time an imaging beam 64 is generated. The frame trigger input 126 is coupled to the reset of the counter 144, so that the counter is reset to "0" once the transducer array 60 completes an imaging cycle. The processing circuitry 120 further comprises a first latch 146 for latching in the current count from the counter 144. The output of the maximum peak detector 142 is coupled to the control input of the first latch 146, so that it outputs the current count each time the amplitude of the currently received imaging beam signal is greater than the currently stored maximum amplitude (the maximum peak detector 142 outputs a logical high).

The processing circuitry 120 further comprises a second latch 148 coupled to the output of the first latch 146 for latching in the count outputted from the first latch 146. The frame trigger input 126 is coupled to the control input of the second latch 148, so that the second latch 148 outputs the final count to the intersecting scan line output 128 once the transducer array 60 completes a full cycle. This count represents the scan line that intersects the respective positioning transducer 36. For example, if the count is 125, the scan line 66 that intersects that respective positioning transducer 36 will be the 125st scan line 66.

The scan tine processing circuitry 120 further comprises another counter 150, the reset of which is coupled to the transmit trigger input 124, such that it is reset to begin counting from zero each time an imaging beam 64 is transmitting by the transducer array 60. Thus, the running count value of the counter 150 provides a measure of time from the transmission of the imaging beam 64. The processing circuitry 120 further comprises a third latch 152 coupled to the output of the counter 150, thereby receiving the count value. The control of the third latch 152 is also coupled to the output of the maximum peak detector 142 to receive a signal indicating whether a maximum peak has been received, i.e., a high if the amplitude of the current peak is greater than the previous stored maximum peak, and a low otherwise. Thus, upon receipt of a high from the maximum peak detector 142, the third latch 152 outputs the count, thereby providing a distance measurement between the transducer array 60 and the positioning transducer 36 in the form of an elapsed time between the transmission and detection of the respective imaging beam 64. Thus, the third latch 152 will only output the count corresponding to a received imaging beam signal that currently has the highest amplitude.

The processing circuitry 120 further comprises a fourth latch 154 coupled to the output of the third latch 152 for latching in the count outputted from the third latch 152. The frame trigger input 126 is coupled to the control input of the fourth latch 154, so that the fourth latch 154 outputs the final count to the transit time output 130 once the transducer array 60 completes a full imaging cycle. This count provides a distance measurement between the transducer array 60 and the positioning transducer 36 in the form of an elapsed time between the transmission and detection of the intersecting imaging beam 64.

D. Registration Processor

Referring back to FIG. 1, the registration processor 46 comprises a (1) global registration subprocessor 114 configured for registering the positioning transducers 36 within the global coordinate system; and (2) a local registration subprocessor 116 configured for registering the positioning transducers 36 within the local imaging coordinate system.

1. Global Registration Sub-Processor

In performing its registration function, the global registration subprocessor 114 first determines the distances between all of the positioning and reference transducers 36 and 38 based on the transit time matrix illustrated in FIG. 5 and a simple distance equation. For example, referring to FIG. 9, a transmitting transducer TX and four receiving transducers RX(1)–(4) are shown being separated from each other by respective distances $d_a$–$d_d$. To measure the distances $d_a$–$d_d$ between the transmitting transducer TX and the receiving transducers RX(1)–(4), the equation d=vt can be used, where v is the velocity of the ultrasound pulse transmitted by the transmitting transducer TX through the medium to the receiving transducers RX(1)–(4), and t is the time that it takes for the ultrasound pulse to travel between the transmitting transducer TX and the respective receiving transducer RX. To simplify the distance computation, the velocity of the ultrasound pulses may be assumed to be constant. This assumption typically only produces a small error, since the velocity of ultrasound pulses (estimated to be 1540 m/s) varies little in solid body tissue and blood.

Once the distances are known, the global registration subprocessor 114 then establishes the global coordinate system by triangulating the relative distance calculations between each reference transducer 38 and the remaining reference transducers 38. The global registration subprocessor 114 then determines the coordinates of the positioning transducers 36 within this global coordinate system by triangulating the relative distance calculations between each of the positioning transducers 36 and the reference transducers 38. Preferably, the registration processor 46 determines the positions of the positioning transducers 36 continually and in real time. In the illustrated embodiment, these positions are determined 15 times/second.

Additional details on this global registration technique can be found in U.S. Pat. No. 6,490,474 and U.S. patent application Ser. No. 09/128,304, entitled "A dynamically alterable three-dimensional graphical mode of a body region," which have previously been incorporated herein by reference.

2. Local Registration Subprocessor

In performing its registration function, the local registration subprocessor 116 first determines angular coordinates in azimuth ($\theta$) and elevation ($\phi$) of each positioning transducer 38 within the local imaging coordinate system by determining the respective imaging scan line that intersects each of the reference transducers 38. In particular, upon receipt of the frame trigger from the imaging control/processing circuitry 32, i.e., at the end of the imaging cycle, the local registration subprocessor 116 acquires the peak amplitude count values from the output 90 of the scan line calculation circuitry 44 and determines the greatest peak amplitude. The particular scan line 66 that corresponds with the greatest amplitude value is deemed to be the scan line 66 that intersects the respective positioning transducer 36. In the alternative case where the scan line processing circuitry 120 is used, the single count value acquired from this circuitry will already indicate the intersecting scan line 66. In either event, the local registration subprocessor 116 will deem the angular coordinates corresponding with the intersecting scan line 66 to be the angular coordinates of the respective positioning transducer 36 within the local imaging coordinate system.

Figure 10:
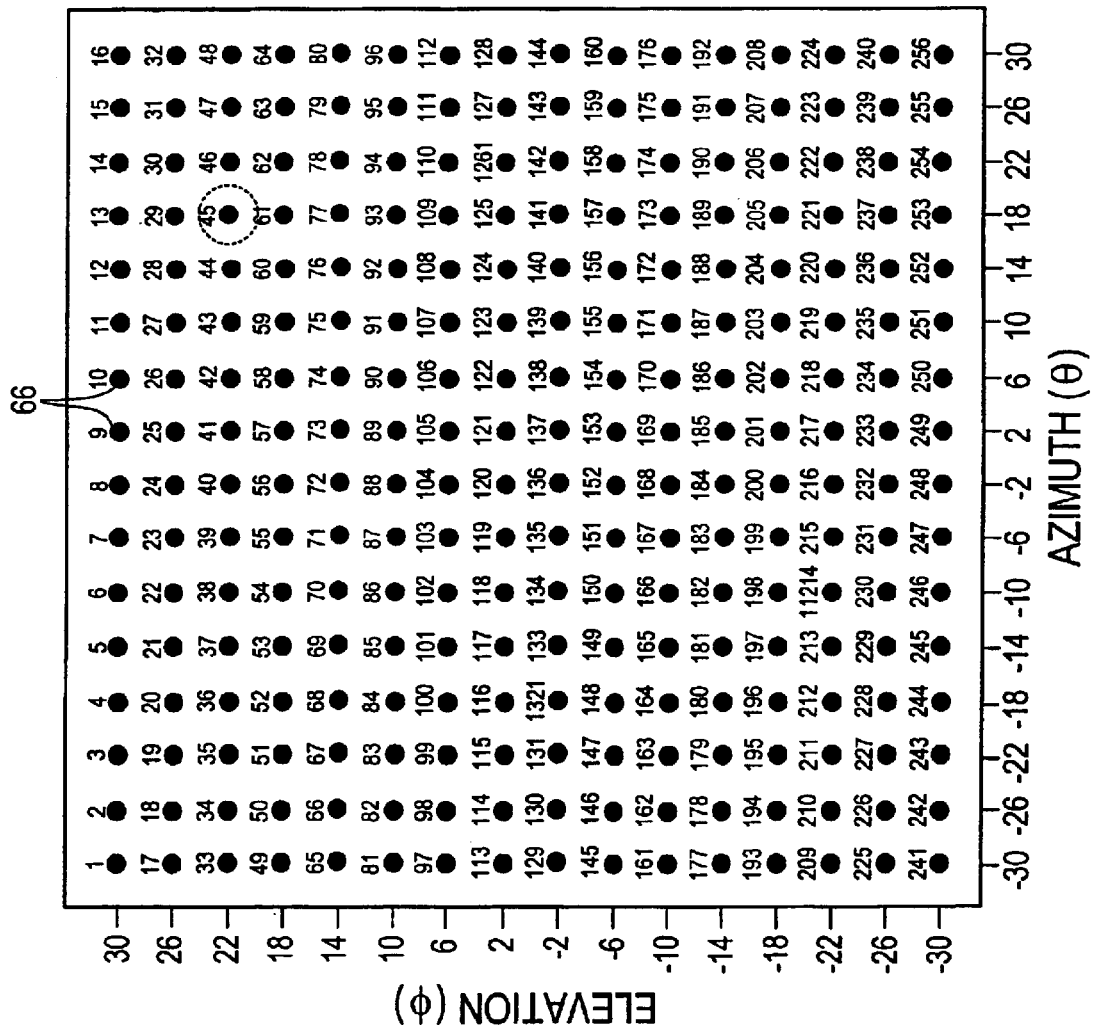
FIG. 10 is a end view of scan lines used by the imaging subsystem illustrated in FIG. 1.

For example, FIG. 10 illustrates the scan lines 66 and their corresponding angular coordinates in the azimuth and elevation. Assuming that the scan lines 66 are numbered, such that the transducer array 60 scans left to right and top to bottom, and assuming that the $45^{th}$ scan line intersects the respective positioning transducer 36, the angular coordinates will be calculated as 18 degrees in the azimuth and 22 degrees in the elevation.

The local registration subprocessor 116 also determines the radial coordinate (r) of each positioning transducer 38 within the local imaging coordinate system. In particular, the local registration subprocessor 116 acquires the transit times from the output 92 of the scan line processing circuitry 44 and identifies the transit time corresponding to the greatest peak amplitude, i.e., the intersecting scan line 66. The local registration subprocessor 116 calculates the distance between transducer array 60 and the respective positioning transducer 36 from this transit time and the distance equation d=vt. This calculated distance represents, the length of the intersecting scan line 66 between the transducer array 60 and the respective positioning transducer 36, and thus is the radial coordinate r of the respective positioning transducer 36 within the local imaging coordinate system.

It should noted that the resolution of the afore-described method is limited to the beam width, i.e., 4×4 degrees. This resolution, however, can be increased by utilizing an optional method to analyze unique receive profiles, each of which is generated by a combination of the 256 imaging beams 64. In particular, the ultrasound field defined by all of the transmitted scan lines 66 creates a unique receive profile at every spatial location in the scanned pyramidal volume. Based on this, expected receive profiles can be stored in a look-up matrix and subsequently compared to measured data to improve the resolution beyond that of the 4 degree scan line spacing. In the preferred embodiment, the expected receive profiles are simulated using the ultrasound simulation program FIELD II Version 2.60 to characterize positions every 1 degree in the azimuth and elevation at a fixed radial distance r, e.g., 70 mm. Due to the transducer array's 60 broad beamwidth and fixed focus, the unique receive profiles will scale with the radial distance r without significant changes. Thus, 4225 different receive signatures made up of 256 data points each will be stored in the look-up matrix along with the corresponding angular coordinates.

Once the peak amplitudes of the 256 scan lines 66 are acquired from the scan line processing circuitry 44, they can be compared with the unique receive profiles in the look-up table to obtain the angular coordinates ($\theta$, $\phi$) of the respective positioning transducer 36 within a 1 degree resolution. Specifically, a cross correlation is performed on the measured and stored data. The unique receive profile that has the highest correlation value with the measured data (i.e., the measured peak amplitudes) indicates the angular coordinates of the respective positioning transducer 36. The equation below sets forth the normalized spatial cross correlation values:

$$\rho(\phi_r, \theta_s) = \frac{\sum_{i=1}^{16}\sum_{j=1}^{16}(S_{ij,rs})(C_{ij})}{\sqrt{\sum_{i=1}^{16}\sum_{j=1}^{16}(S_{ij,rs})^2 \sum_{i=1}^{16}\sum_{j=1}^{16}(C_{ij})^2}}$$

where
$$S_{ij,rs} = Psim_{\phi,\theta}(\phi_i, \theta_j) - \overline{Psim_{\phi,\theta}}$$
$$C_{ij} = Pmeas(\phi_i, \theta_j) - \overline{Pmeas}$$

$Psim_{\phi_r, \theta_s}$ is the peak-to-peak detected signal amplitude from the simulated receive profiles; $\phi_r$ and $\theta_s$ denote the angular position of the simulated positioning transducer; r and s correspond to 4225 unique positions, $\overline{Psim_{\phi_r, \theta_s}}$ is the mean value for the receive profile at the angular position corresponding to (r, s); Pmeas is the detected signal amplitude from the actual positioning transducer; $\phi_i$ and $\theta_j$ are the angles corresponding to each of the 256 scan lines in one image frame; $\overline{Pmeas}$ is the mean value for the actual positioning transducer's receive profile. The cross correlation values are stored in the matrix $\rho(\phi_r, \theta_s)$, where $\phi_r$ and $\theta_s$ are the angular positions in the elevation and azimuth for the simulated positioning transducer positions. The angular position corresponding to the highest correlation value in matrix $\rho(\phi_r, \theta_s)$ indicates the position closest to the actual positioning transducer's location within 1 degree.

As a further improvement on the resolution, two one-dimensional splines through the five highest correlation values in the azimuth and elevation can be used to refine the location of the positioning transducer 36.

E. Coordinate System Transformer

Referring back to FIG. 1, the coordinate system transformer 48 is transforming the local coordinate system into the global coordinate system. In performing its transformation function, the coordinate system transformer 48 calculates a transform based on the Cartesian coordinates (x, y, z) of the positioning transducers 36 within the global coordinate system, as calculated by the global registration subprocessor 114, and the spherical coordinates (r, $\theta$, $\phi$) of the positioning transducers 36 within the local imaging coordinate system, as calculated by the local registration subprocessor 116. This can be accomplished using conventional transform techniques. For example, the coordinate system transformer 48 can first transform the local spherical coordinates (r, $\theta$, $\phi$) of the positioning transducers 36 into local Cartesian coordinates (x', y', z'). Then, letting (P1, P2, P3) be the position of the positioning transducers 36 in the global coordinate system, and (P1', P2', P3') be the position of the positioning transducers 36 within the local coordinate system, the Procruste's Transform can be used to calculate a transform T that transforms the local coordinate system (x', y', z') into the global coordinate system (x, y, z). As previously discussed, the imaging control/processing circuitry 32 uses this transform T to register the acquired image data, which is stored in the local Cartesian coordinate system (x', y', z'), within the global coordinate system (x, y, z).

It should be noted that only three positioning transducers 36 are initially required to be illuminated by the transducer array 60 in order to register the image data within the global coordinate system. If it is assumed that only the angle of the transducer array 60 moves after calculation of the transform and initial registration of the image data within the global coordinate system, i.e., the positional coordinates of the center of the transducer array 60 will not move, only two positioning transducers 36 will be required to be illuminated by the transducer array 60 in order to properly register the image data within the global coordinate system. The center of the transducer array 60 forms the third common point between the two coordinate systems, and then the local coordinate system can be transformed into the global coordinate system as previously described.

IV. 3-D Rendering Processor

The 3-D graphical processor 18 is configured for generating a global representation of an internal anatomical structure in the form of a computer-generated representation (i.e., a reconstruction) of the heart chamber within the global coordinate system. The 3-D graphical processor 18 accomplishes this by acquiring the positions of the positioning transducers 36 within the global coordinate system as the mapping/ablation catheter 24 is moved around within the cavity of the internal anatomical structure, and then deforming an anatomical shell to the acquiring positions. The 3-D graphical processor 18 is also configured to construct a graphical representation of the mapping/ablation catheter 24 within the graphical representation of the internal anatomical structure based on the calculated positional coordinates of the positioning transducers 36 located at the distal end of the catheter 24 and the known positional relationship between the positioning transducers.

The 3-D graphical processor 18 is also configured for superimposing an electrical activity map over the graphical representation of the internal anatomical structure based on the electrical activity information acquired from the mapping/ablation subsystem 12. This electrical activity map illustrates sites of interest, e.g., electrophysiology recording and ablation sites, for providing subsequent ablative treatment. Additional details on this graphical reconstruction technique can be found in U.S. Pat. No. 6,490,474 and U.S. patent application Ser. No. 091128,304, entitled "A dynamically alterable three-dimensional graphical mode of a body region," which have previously been incorporated herein by reference.

Instead of, or in addition to, graphically reconstructing the body tissue, any one of a number of imaging techniques to generate a 3-D image of the body tissue. For example, a Magnetic Resonance Imaging (MRI) imager, or a Computed Tomography (CT) imager can be used to generate a 3-D image of the internal anatomical structure. To accomplish this, the imager may be moved laterally and/or rotationally to obtain multiple cross-sectional or sector images of the body tissue at different positions within the body tissue. The multiple cross-sectional images may then be aggregated (i.e., pieced together) to reconstruct a 3-D image of the internal anatomical structure. The 3-D image of the internal anatomical structure may be registered within the global coordinate system by tracking the position of the imager, and therefore the cross-sectional or sector images taken by the imager, for example, by attaching ultrasound positioning transducers to the imager. Alternatively, the position of anatomic landmarks within the body tissue may be determined in the global coordinate system, e.g., using the mapping/ablation catheter 24. The 3-D image of the internal anatomical structure may then be registered with the global coordinate system by correlating the positions of the anatomic landmarks in the 3-D image of the internal anatomical structure with the determined positions of the anatomic landmarks in the global coordinate system.

V. Composite Image Generator

The composite image generator 20 is configured for superimposing the registered image data obtained from the image control/processing circuitry 32 over the 3-D graphical information obtained from the 3-D graphical processor 18, and displaying the composite image data on the display 22 as a composite image of the internal anatomical structure. This can be accomplished using graphical techniques well known in the art.

VI. Alternative Embodiment of Medical Treatment System

Figure 11:
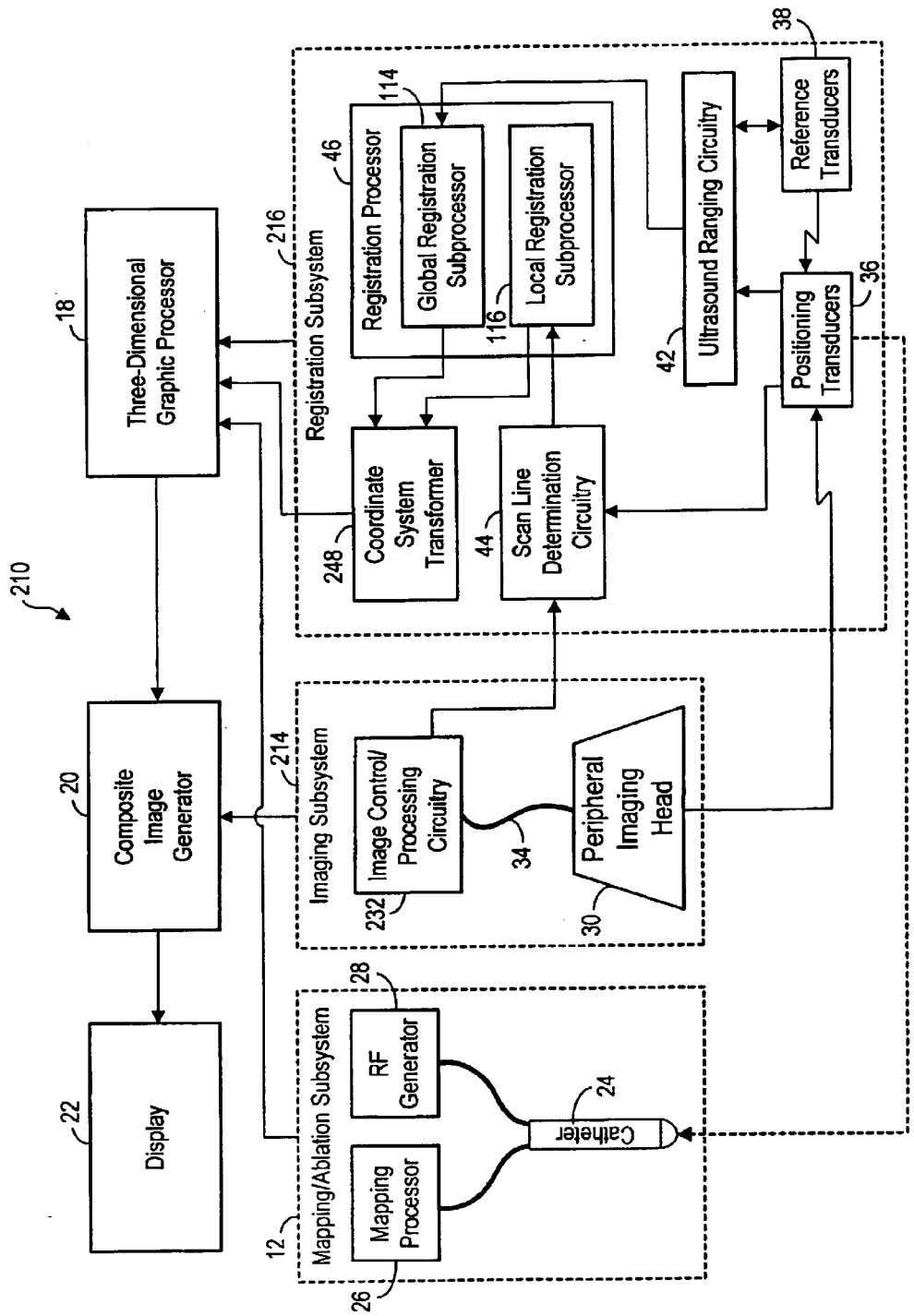
FIG. 11 is a functional block diagram of another preferred embodiment of a medical treatment system constructed in accordance with the present inventions.

Referring to FIG. 11, another exemplary medical treatment system 210 constructed in accordance with the present inventions is shown. The treatment system 210 is similar to the previously described treatment system 10, with the exception that the coordinates of the three-dimensional graphical information, rather than that of the image data, is transformed so that the composite data is displayed within the local coordinate system rather than the global coordinate system.

To this end, the treatment system 210 comprises an imaging subsystem 214 that is similar to the previously described imaging subsystem 214 with the exception that it includes image control/processing circuitry 232 that merely transforms the image data acquired by the peripheral imaging head 30 from a local spherical coordinate system into a local Cartesian coordinate system, and outputs this image data to the composite image generator 20. The imaging subsystem 214 does not transform image data into the global Cartesian coordinate system, because the image data will actually be displayed within the local coordinate system. Rather, the treatment system 210 includes a 3-D graphical processor 218 that, like the previously described 3-D graphical processor 18, generates graphical information, but additionally transforms this information from the global Cartesian coordinate system into the local Cartesian coordinate.

The treatment system 210 also comprises a registration subsystem 216 that is similar to the previously described registration subsystem 16, with the exception that it includes a coordinate system transformer 248 that transforms the global coordinate system into the local coordinate system, rather than the other way around. In performing its transformation function, the coordinate system transformer 248, like the previously described coordinate system transformer 48, calculates a transform based on the Cartesian coordinates $(x, y, z)$ of the positioning transducers 36 within the global coordinate system, as calculated by the global registration subprocessor 114, and the spherical coordinates $(r, \theta, \phi)$ of the positioning transducers 36 within the local imaging coordinate system, as calculated by the local registration subprocessor 116. When using the Procruste's Transform, however, the coordinate system transformer 248 calculates a transform T that transforms the global coordinate system into the local coordinate system by transforming the local spherical coordinates $(r, \theta, \phi)$ of the positioning transducers 36 into local Cartesian coordinates $(x, y, z)$, and letting (P1, P2, P3) be the position of the positioning transducers 36 in the local coordinate system, and (P1', P2', P3') be the position of the positioning transducers 36 within the global coordinate system. The three-dimensional graphical processor 218 will then use this transform T to transform the graphical information, which is stored in the global Cartesian coordinate system $(x', y', z')$, into the local coordinate system $(x, y, z)$.

The composite image generator 20 will then superimpose the image data obtained from the image control/processing circuitry 232 over the 3-D graphical information obtained from the 3-D rendering processor 218, and displaying the composite image data on the display 22 as a composite image of the internal anatomical structure.

Although particular embodiments of the present invention have been shown and described, it will be understood that it is not intended to limit the present invention to the preferred embodiments, and it will be obvious to those skilled in the art that various changes and modifications may be made without departing from the spirit and scope of the present invention. Thus, the present inventions are intended to cover alternatives, modifications, and equivalents, which may be included within the spirit and scope of the present invention as defined by the claims.

What is claimed is:

1. A method of imaging an internal anatomical structure, comprising:

acquiring ultrasound image data of the anatomical structure within a first coordinate system;

determining a location of at least one ultrasound transducer within the first coordinate system;

determining a location of the at least one ultrasound transducer within a second coordinate system;

performing a transformation between the first and second coordinate systems based on the determined locations of the at least one ultrasound transducer within the respective first and second coordinate systems.

2. The method of claim 1, wherein one or both of the first and second coordinate systems is a three-dimensional coordinate system.

3. The method of claim 1, wherein both of the first and second coordinate systems are three-dimensional coordinate systems.

4. The method of claim 1, wherein the first and second coordinate systems are respective local and global coordinate systems.

5. The method of claim 1, wherein the first coordinate system is a spherical coordinate system, and the second coordinate system is a Cartesian coordinate system.

6. The method of claim 1, wherein the second coordinate system is fixed relative to the anatomical structure.

7. The method of claim 1, wherein the first coordinate system is transformed into the second coordinate system.

8. The method of claim 7, wherein ultrasound image data is registered in the second coordinate system in accordance with the coordinate system transformation.

9. The method of claim 8, further comprising displaying the registered ultrasound imaging data as an ultrasound image of the anatomical structure.

10. The method of claim 9, further comprising generating and registering graphical information within the second coordinate system, and displaying the registered graphical information together with the ultrasound image.

11. The method of claim 1, wherein the second coordinate system is transformed into the first coordinate system.

12. The method of claim 11, further comprising generating and registering graphical information within the second coordinate system, and registering the graphical information within the first coordinate system in accordance with the coordinate system transformation.

13. The method of claim 12, further comprising displaying the ultrasound imaging data as an ultrasound image of the anatomical structure, and displaying the graphical information together with the ultrasound image.

14. The method of claim 12, further comprising determining the location of an anatomical site of interest, wherein the graphical information represents the anatomical site of interest.

15. The method of claim 14, wherein anatomical site of interest is an ablation site.

16. The method of claim 14, wherein anatomical site of interest is an electrophysiology recording site.

17. The method of claim 1, wherein the ultrasound image data is acquired internally.

18. The method of claim 1, wherein the ultrasound image data is acquired externally.

19. The method of claim 1, wherein the anatomical structure is an organ.

20. The method of claim 1, wherein the anatomical structure is a heart.

21. The method of claim 1, wherein the at least one ultrasound transducer comprises three or more ultrasound transducers.

22. The method of claim 1, wherein the location determination of the at least one ultrasound transducer within the first coordinate system comprises generating one or more ultrasound signals between the at least one ultrasound transducer and at least one reference ultrasound transducer, the at least one reference ultrasound transducer being fixed relative to a location at which the ultrasound image data is acquired.

23. The method of claim 22, wherein the one or more ultrasound signals are transmitted by the at least one reference ultrasound transducer and is used to acquire at least a portion of the ultrasound image data.

24. The method of claim 22, further comprising receiving the one or more ultrasound signals and measuring the amplitudes or transit times of the received one or more ultrasound signals, wherein the location of the at least one ultrasound transducer within the first coordinate system is based at least partially on the one or more measured ultrasound signal amplitudes or transit times.

25. The method of claim 22, wherein the at least one reference ultrasound transducer comprises a plurality of reference ultrasound transducers.

26. The method of claim 1, further comprising moving the at least one ultrasound transducer relative to the anatomical structure.

27. A medical imaging system, comprising:
an imaging subsystem having a peripheral imaging device configured for acquiring ultrasound image data of an internal anatomical structure, the ultrasound image data arranged in a first coordinate system; and
a registration subsystem comprising at least one ultrasound transducer and at least one processor configured for determining a location of at least one ultrasound transducer within the first coordinate system, determining a location of the at least one ultrasound transducer within a second coordinate system, and for performing a transformation between the first and second coordinate systems based on the determined locations of the at least one ultrasound transducer within the respective first and second coordinate systems.

28. The medical imaging system of claim 27, wherein one or both of the first and second coordinate systems is a three-dimensional coordinate system.

29. The medical imaging system of claim 27, wherein both of the first and second coordinate systems are three-dimensional coordinate systems.

30. The medical imaging system of claim 27, wherein the first and second coordinate systems are respective local and global coordinate systems.

31. The medical imaging system of claim 27, wherein the first coordinate system is a spherical coordinate system, and the second coordinate system is a Cartesian coordinate system.

32. The medical imaging system of claim 27, wherein the second coordinate system is fixed relative to the anatomical structure.

33. The medical imaging system of claim 27, wherein the at least one processor is configured for transforming the first coordinate system into the second coordinate system.

34. The medical imaging system of claim 33, wherein the imaging subsystem further comprises an image processor configured for registering the ultrasound image data in the second coordinate system in accordance with the coordinate system transformation.

35. The medical imaging system of claim 34, further comprising a display for displaying the registered ultrasound image data as an ultrasound image of the anatomical structure.

36. The medical imaging system of claim 35, further comprising a graphical processor configured for generating and registering graphical information within the second coordinate system, and the display is for displaying the graphical information together with the ultrasound image.

37. The medical imaging system of claim 27, wherein the at least one processor is configured for transforming the second coordinate system into the first coordinate system.

38. The medical imaging system of claim 37, further comprising a graphical processor configured for generating and registering graphical information within the second coordinate system.

39. The medical imaging system of claim 37, further comprising a display for displaying the ultrasound image data as an ultrasound image of the anatomical structure, and for displaying the registered graphical information together with the ultrasound image.

40. The medical imaging system of claim 27, wherein the peripheral imaging device is an external device.

41. The medical imaging system of claim 27, wherein the peripheral imaging device is an internal device.

42. The medical imaging system of claim 27, wherein the peripheral imaging device is selected from an internal imaging probe consisting of an intracardiac imaging probe and a transesophogeal imaging probe.

43. The medical imaging system of claim 27, wherein the at least one ultrasound transducer comprises three or more ultrasound transducers.

44. The medical imaging system of claim 27, wherein the registration subsystem comprises processing circuitry configured for conditioning the at least one ultrasound transducer to receive an ultrasound signal transmitted by another at least one ultrasound transducer, the other at least one ultrasound transducer being fixed relative to the peripheral imaging device, wherein the processing subsystem is configured for determining the location of the at least one ultrasound transducer within the first coordinate system based on the ultrasound signal transmission.

45. The medical imaging system of claim 44, further comprising an imaging controller configured for conditioning the other at least one ultrasound transducer to transmit the at least one ultrasound signal, wherein the peripheral device comprises the other at least one ultrasound transducer and is configured for acquiring the ultrasound image data using the at least one ultrasound signal.

46. The medical imaging system of claim 44, wherein the processing circuitry is configured for measuring one or more characteristics of the at least one received ultrasound signal, wherein the processing subsystem is configured for determining the location of the at least one ultrasound transducer within the first coordinate system based at least partially on the one or more measured ultrasound signal characteristics.

47. The medical imaging system of claim 44, wherein the other one or more ultrasound transducers comprises a plurality of ultrasound transducers.

48. The medical imaging system of claim 27, wherein the registration subsystem comprises ranging circuitry configured for conditioning the at least one ultrasound transducer to receive ultrasound signals transmitted by a plurality of reference ultrasound transducers, wherein the processing subsystem is configured for determining the location of the at least one ultrasound transducer within the second coordinate system based on the ultrasound signal transmissions.

* * * * *